(12) United States Patent
Marty

(10) Patent No.: US 6,402,683 B1
(45) Date of Patent: Jun. 11, 2002

(54) VAGINAL STIMULATOR AND DEVICE FOR THE TREATMENT OF FEMALE URINARY INCONTINENCE

(76) Inventor: Jean-Claude Marty, 16-21 Bay Rd., #908, Miami Beach, FL (US) 33139

( * ) Notice: Subject to any disclaimer, the term of this patent is extended or adjusted under 35 U.S.C. 154(b) by 0 days.

(21) Appl. No.: 09/505,696

(22) Filed: Feb. 17, 2000

(51) Int. Cl.[7] .................................................. A61F 2/00
(52) U.S. Cl. ...................................................... 600/29
(58) Field of Search ....................... 600/29–31; 601/15; 607/39–41, 115–116, 138

(56) References Cited

U.S. PATENT DOCUMENTS

| | | | |
|---|---|---|---|
| 3,866,613 A | * 2/1975 | Kenny et al. ............... | 607/138 |
| 4,515,167 A | * 5/1985 | Hochman ................ | 607/138 X |
| 4,688,575 A | * 8/1987 | DuVall ..................... | 607/41 X |
| 4,873,996 A | * 10/1989 | Maurer ...................... | 607/138 |
| 4,881,526 A | * 11/1989 | Johnson et al. ............... | 601/15 |
| 5,454,840 A | * 10/1995 | Krakovsky et al. ........... | 607/39 |
| 5,800,501 A | * 9/1998 | Sherlock .................... | 607/138 |
| 5,881,731 A | * 3/1999 | Remes .................... | 607/138 X |
| 5,978,712 A | * 11/1999 | Suda et al. ................... | 607/41 |
| 6,086,549 A | * 7/2000 | Neese et al. ............... | 607/41 X |
| 6,240,315 B1 | * 5/2001 | Mo et al. ...................... | 607/41 |

* cited by examiner

Primary Examiner—John P. Lacyk
Assistant Examiner—Joseph A. Cadugan
(74) Attorney, Agent, or Firm—Connolly Bove Lodge & Hutz LLP

(57) ABSTRACT

A vaginal applicator-stimulator system includes a body having a first set of conductors for transmitting electrical pulses to the vagina. A battery power supply is located inside the stimulator body and a micro-controller is located in the stimulator body for controlling the application of pulsating signals to the first set of conductors in accordance with programmed instructions corresponding to a particular type of urinary incontinence to be treated. A case is included for enclosing the cylindrical stimulator body during non-use of the stimulator body, the case having-contacts correspondingly aligned with the conductors of the stimulator body. An apparatus is located in the case for entering instructions regarding current to be applied by the first set of conductors of the stimulator body that stimulate according to the type of urinary incontinence to be treated. The micro-controller in the stimulator body stores the entered instructions.

5 Claims, 3 Drawing Sheets

VAGINAL STIMULATOR AND DEVICE FOR THE TREATMENT OF FEMALE URINARY INCONTINENCE

BACKGROUND OF THE INVENTION

1. Field of the Invention

The present invention relates to a vaginal stimulator and a device for the treatment of female urinary incontinence by the way of electrical stimulation applied to the pelvic floor musculature and surrounding structures.

2. Description of the Prior Art

Female urinary incontinence is a condition with severe economic and psychosocial impact. There are several types of urinary incontinence but all are characterized by an inability to restrain urinary voiding. The three most frequent types of urinary incontinence are the stress incontinence, characterized by the involuntary loss of urine from the urethra during physical exertion, the urge incontinence or involuntary loss of urine associated with an abrupt and strong desire to void, and the mixed urinary incontinence which results from both urge incontinence and stress incontinence.

Various methods have been propesed for improving the strength and tone of the pelvic floor muscle group. In 1948, Arnold Kegel described pelvic floor exercises as a treatment option in stress incontinence and invented a set of exercises to strengthen and support the pelvic floor. The purpose of the Kegel exercises is to increase volume and to develop stronger reflex contractions following quick rise in intra-abdominal pressure. Many women find these Kegel exercises difficult and uncomfortable to perform and the major obstacle to success with Kegel exercises is the tendency among women to give up or forget how to correctly do the exercises.

Electrical stimulation of the pelvic floor is an effective therapy both for stress incontinence and urge incontinence. Electrical stimulation of the pelvic floor automates Kegel exercises through the use of direct electrical stimulation of the vagina and bladder muscle. Electrical stimulation of the pelvic floor to treat stress incontinence and urge incontinence was first studied in the early 1960's and clinical studies from the 70's through 90's have reaffirmed its effectiveness.

With the first electrical stimulation methods used to treat female urinary incontinence, women had to go in a medical setting to undergo electrical stimulation session of their pelvic floor muscle. Later electrical stimulators for home treatment appeared. These devices are usually in two parts: an inside vagina part which is a vaginal plug with electrodes intended to be in contact with the vagina wall and an outside vagina part which can be the pulse generator and a power supply or a power supply only if the pulse generator is inside the vaginal plug. Such devices are not convenient because of the cable(s) between the inside vagina part and the outside vagina part. Moreover, hygiene problems are encountered when the vaginal plug has not been completely cleaned before its insertion in the vagina.

Other devices are used with a special condom which must be disposed of and changed after each use.

Said devices of the prior art are not well accepted by the women because they are exacting and difficult to use. With some devices the insertion and the extraction of the plug are not easy, the presence of cables and/or cumbersome equipment is not comfortable, the plugs are difficult to clean, the user must have batteries in advance, and in the case of devices used with condoms the user must have condoms in advance. There is then a need for a pelvic floor muscle electrical stimulation device effective, convenient to use and easy to insert, extract and clean.

SUMMARY OF THE INVENTION

The present invention is directed to a vaginal stimulator with a body adapted to be inserted in women's vagina to electrically stimulate the pelvic floor musculature and surrounding structures, comprising a battery as power supply, means for applying preprogrammed instructions concerning the current frequency adapted to the type of incontinence to be treated and the treatment duration.

Advantageously, said means for applying preprogrammed instructions comprise a microcontroller to select the pulse frequency and the working time given by an outer electronic control system. In a preferred embodiment of the invention, said electronic control system is located in a case comprising a housing for said stimulator, when not in use.

Preferably, said vaginal stimulator body comprises on its surface, at least two sets of conductors, a first set being used as electrodes to transmit electrical pulses to the pelvic floor musculature, and a second set, which, jointly with the first one, is able to transmit the instructions of the operator to the vaginal stimulator microcontroller.

Said vaginal stimulator is advantageously watertight.

It is convenient that an eyelet be provided at one end of the vaginal stimulator body, with a guide to thread a string into the eyelet.

The invention is also directed to a device for the treatment of female urinary incontinence by electrical stimulation applied to the pelvic floor musculature and surrounding structures, comprising a vaginal stimulator as above defined and a carrying and control case, without cable linking one to the other.

In a preferred embodiment, the carrying and control case comprises a housing for said vaginal stimulator, a transformer with charge circuitry to charge the vaginal stimulator battery, an electronic control system to transmit the instructions given by the operator.

Said housing is advantageously provided with metal contacts arranged to be in contact with the conductors of the vaginal stimulator when put into the housing.

It further comprises a wedge adapted to go into the vaginal stimulator eyelet and intended to secure the position of the vaginal stimulator in the housing so that the conductors of the vaginal stimulator be always in contact with the corresponding metal contacts of the housing.

The above instructions are given by the operator to the vaginal stimulator microcontroller through control knobs.

The programmable vaginal stimulator of the present invention is very convenient and easy to use. Between each use the rechargeable battery of the vaginal stimulator is recharging when the vaginal stimulator is in its housing and the cover of the carrying and control case is closed. Before each use the user has only to select the type of incontinence and program the use time. Usually, this programming is done once and for all before the first use. After having thread a piece of string through the eyelet of the vaginal stimulator with the help of the guide string, the user can lubricate the vaginal stimulator to make easier its insertion in the vagina. Then the vaginal stimulator is inserted into the vagina like a tampon, just so it disappears into the vaginal opening. When the use time is passed, the device user takes out the vaginal stimulator from the vagina, cuts the string, throws it away, cleans the vaginal stimulator with mild soap or alcohol, or other disinfectants, wipes it, places it back in its resting nest and closes the cover of the carrying and control case. The battery will recharge automatically.

DETAILED DESCRIPTION

Figure 1:
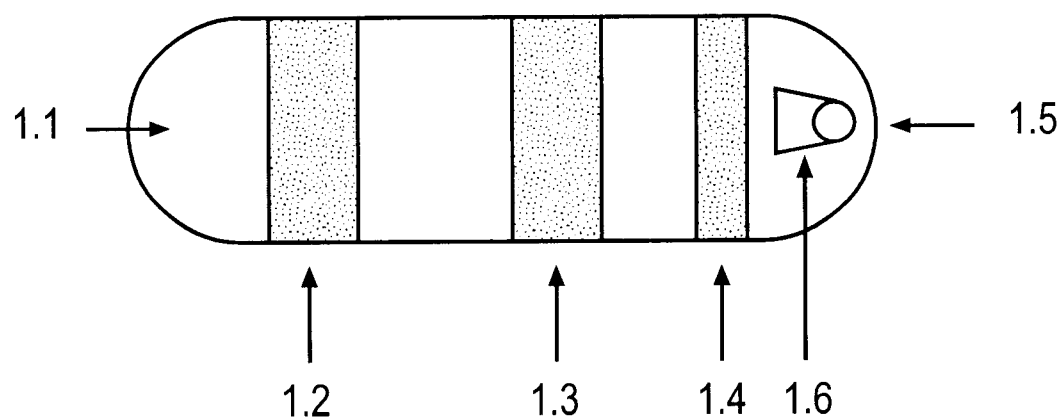
FIG. 1 is a view of the vaginal stimulator according to the invention.

FIG. 1 illustrates a vaginal stimulator according to the invention. Said vaginal stimulator (1.1) is composed of a cylinder-shaped, polymer material body with two rounded ends. Such a stimulator may, for example, have the following dimensions: length 8 centimeters, diameter 2.5 centimeters.

Figure 2:
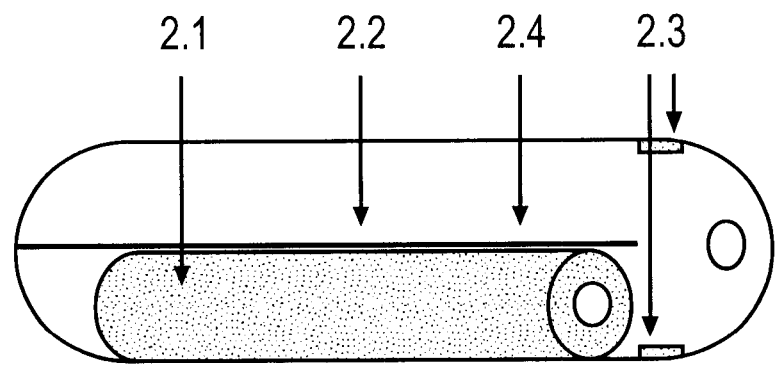
FIG. 2 is an exploded view of the inside of the vaginal stimulator.

The vaginal stimulator (1.1), which comprises a division floor (2.4), includes the following elements:

1. Three conductors (1.2), (1.3), (1.4) which are included in the exterior polymer material body surface. Two of the three conductors are used as electrode +(1.2) and electrode− (1.3) to carry the electric pulses coming from an inside vaginal stimulator microcontroller (FIG. 2: (2.2)) to the vaginal musculature when the vagina stimulator is operating. Two of the three conductors (1.2), (1.4) are used to charge the inside vaginal stimulator rechargeable battery (FIG. 2: (2.1)) and said three conductors (1.2), (1.3), (1.4) are used to transmit instructions to the inside vaginal stimulator microcontroller (FIG. 2: (2.2)) when the device user is programming the vaginal stimulator.

2. An eyelet (1.5) for string connection. An about 20 centimeters bit of string is threaded through the vaginal stimulator eyelet (1.5) and the two ends of the string are knotted before the use of the vaginal stimulator. This bit of string enables an, easier extraction of the vaginal stimulator at the end of the use time.

3. A string guide (1.6) to easier thread the string in the vaginal stimulator eyelet (1.5).

4. A rechargeable battery (2.1) which is the power supply of the vaginal stimulator (1.1). This rechargeable battery is charged through two conductors (1.2), (1.4) of the vaginal stimulator (1.1) and two corresponding metal contacts of an outside device, advantageously of a carrying and control case adapted for housing the vaginal stimulator.

5. A microcontroller (2.2) with microprocessor, random access memory and input output system, to generate the electric pulses necessary to make working the vaginal stimulator (1.1) and execute the different orders given by the operator.

6. An inside round seal (2.3) which permits to make the vaginal stimulator watertight and easy to clean with mild soap, alcohol or other disinfectants.

Figure 4A:
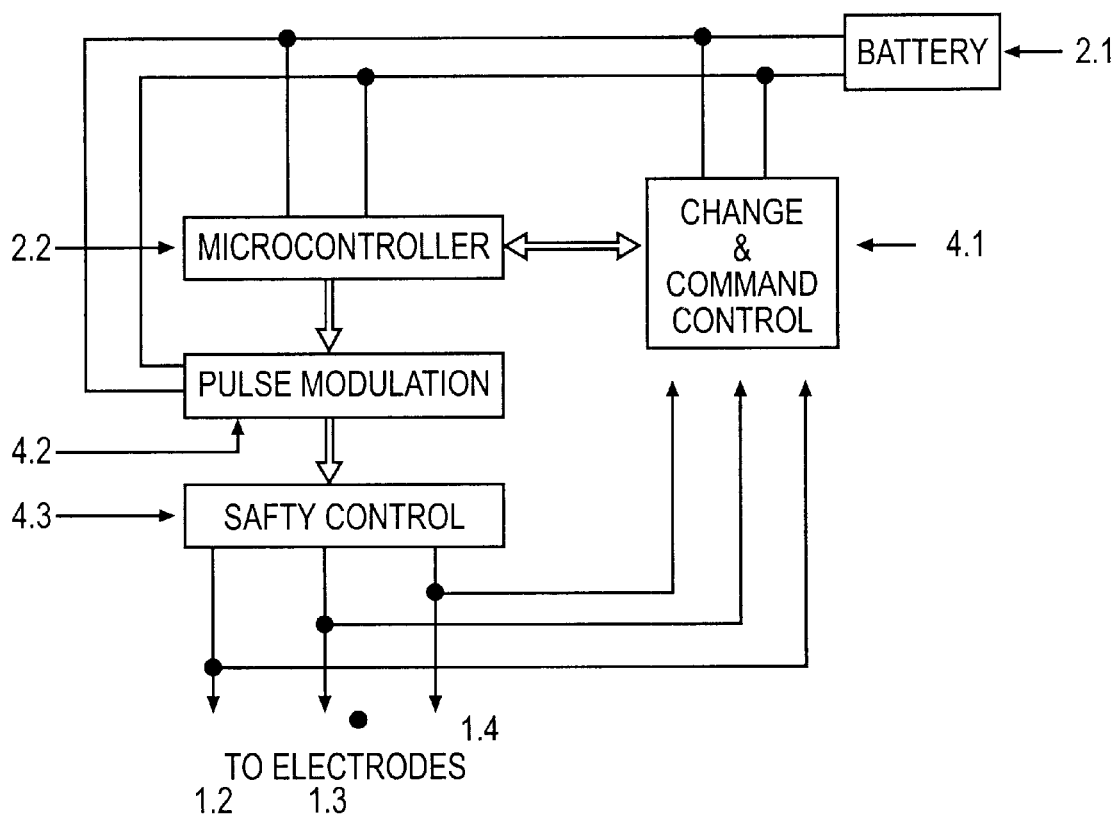
FIG. 4A is a block diagram illustrating the inside stimulator electronic circuit.

The block diagram of the inside stimulator electronic circuit is given on FIG. 4A. As above-mentioned, the microcontroller (2.2), supplied by the battery (2.1) and in connection with a charge and command control (4.1), generates electric pulses which through a pulse modulation system (4.1) and a safety control system (4.3) are transmitted to the electrodes (1.2), (1.3) and the third conductor (1.4). Said electrodes and conductor are then used to charge the battery (2.1).

In a preferred embodiment, said vaginal stimulate is provided with a carrying and control case.

The carrying and control case may have a rectangle parallepipede shape and comprises a main body with a cover, which may be together joined by a hinge. Said case has, for example, the following dimensions: 10 centimeters long, 10 centimeters wide and 5 centimeters high. It is divided in two parts: the main body (3) which may be 10 centimeters long, 10 centimeters wide and 4 centimeters high and the cover (not represented) which may have, for example, the following dimensions: 10 centimeters long, 10 centimeters wide and 1 centimeter high.

Figure 3:
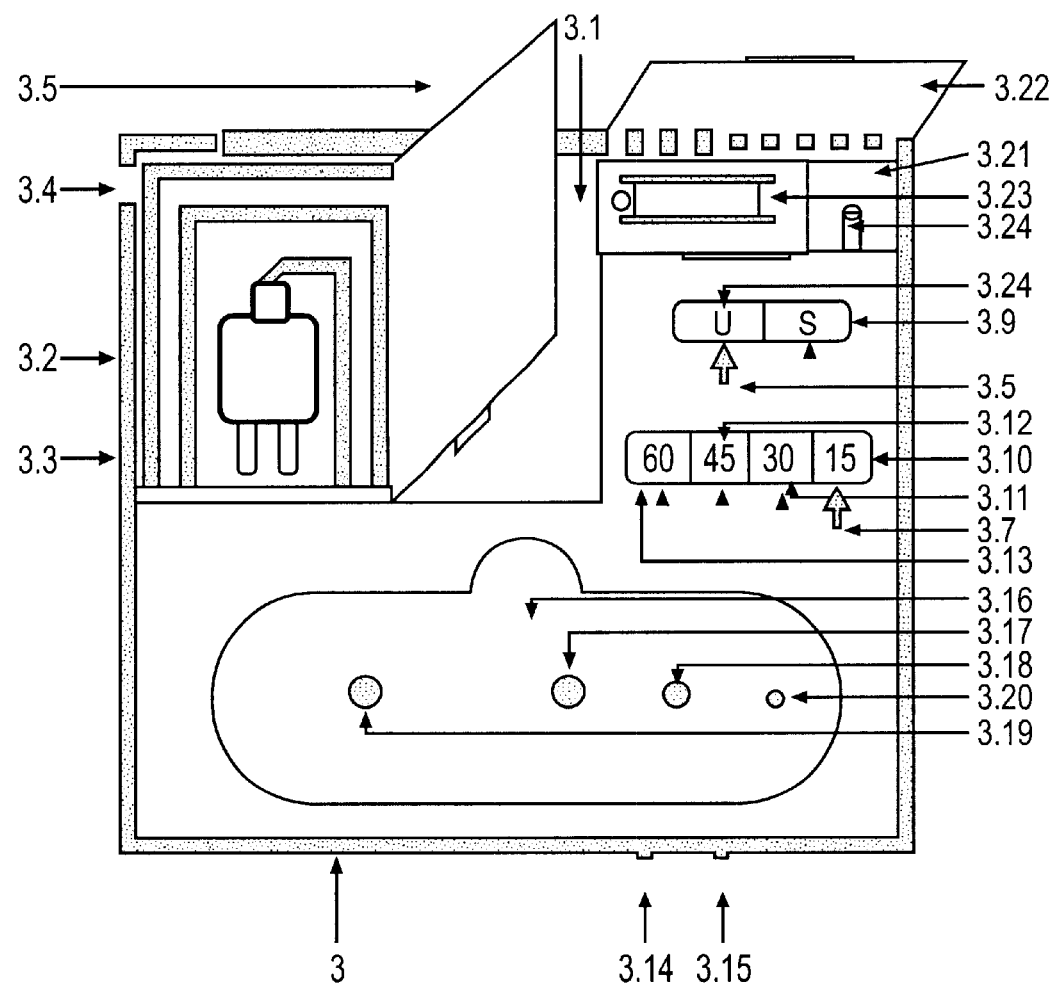
FIG. 3 is a view from the inside of a carrying and control case, intended for containing a vaginal stimulator.

The main body includes the following elements illustrated on FIG. 3:

1. A transformer with charge circuitry located in compartiment (3.1) of the main body which receives equally input current of 110 or 220 volts and will transform it in an adequate output current able to charge the inside vaginal stimulator rechargeable battery for example in 4 to 6 hours.

2. A power cord (3.2) to link the transformer to the supply area. This power cord is located in compartment (3.3) and is directly connected to the transformer. The power cord can be easily gotten out of its location (3.3) to be connected with the mains supply. Once the power cord out of its location and the power cord location cover (3.5) closed, the power cord will be hold in a passage (3.4) and the cover of the carrying and control case can be closed.

3. An electronic control system (not represented) permitting to the device user, through the two control knobs (3.6), (3.7) and the carrying and control case cover, to transmit orders to the vaginal stimulator microcontroller or to recharge the inside vaginal stimulator rechargeable battery.

4. Control knob (3.6) permits to the device user to select the type of urinary incontinence: urge incontinence (3.8) or stress incontinence (3.9). The urge incontinence position (3.8) corresponds to 12.5 Hz pulse frequency and the stress incontinence position (3.9) corresponds to 50 Hz pulse frequency coming from the inside vaginal stimulator microcontroller. The orders given by the device user through this control knob (3.6) are sent to the electronic control system of the carrying and control case.

5. Control knob (3.7) permits to the device user to select the use time of the vaginal stimulator: 15 minutes (3.10), 30 minutes (3.11), 45 minutes (3.12) or 60 minutes (3.13). The orders given by the device user to the control knob (3.7) are sent to the electronic control system of the carrying and control case.

6. A green control light (3.14) which indicate to the device user that the inside vaginal stimulator rechargeable battery is fully charged and that the vaginal stimulator can be used. When this green control light (3.14) is on, the red control light (3.15) is off 7. A red control light (3.15) which indicates to the device user that the inside vaginal stimulator rechargeable battery is always in charge and that the vaginal stimulator cannot yet be used. When this red control light (3.15) is on, the green control light (3.14) is off.

8. A housing (3.16) wherein the vaginal stimulator (1.1) can be put between each use. Said housing has the same shape than the vaginal stimulator but a slight upper size to permit to the vaginal stimulator to fit easily into the housing. The bottom of housing (3.16) comprises three metal contacts (3.17), (3.18), (3.19) intended for transmitting to the three vaginal stimulator conductors (FIG. 1: (1.2), (1.3), (1.4)), orders coming from the electronic control system and given by the device user through the control knobs (3.6), (3.17) or through the carrying and control case cover. A wedge (3.20) is provided at one end of the housing (3.16) and is adapted to fit into the vaginal stimulator eyelet (1.5)) when the vaginal stimulator is put into the housing (3.16). The wedge (3.20) is intended to maintain the vaginal stimulator in its location and to secure that the three metal contacts (3.17), (3.18), (3.19) of the housing (3.16) be in connection with the three vaginal stimulator conductors (1.2), (1.3), (1.4) when the vaginal stimulator is in the housing.

9. A string spool niche (3.21) with a cover (3.22) intended to keep a string spool (3.23). A cutting system (3.24) is provided with the string pool niche to cut the string before the use or after the use of the vaginal stimulator.

10. In the hinge joining the cover to the main body of the carrying and control case there is a switch which gives orders to the electronic control system. The opening of the cover stops automatically the charge of the inside stimulator rechargeable battery and starts the working of the vaginal stimulator, when the vaginal stimulator is in its housing. The closing of the cover stops automatically the working of the vaginal stimulator and starts the charge of the inside vaginal stimulator rechargeable battery, when the vaginal stimulator is in its housing.

Figure 4B:
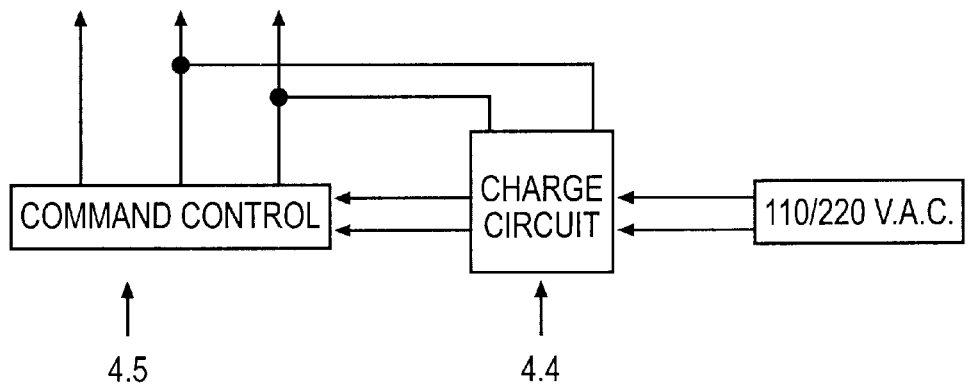
FIG. 4B is a block diagram illustrating the inside carrying and control case electronic control system.

The block diagram of the inside carrying and control case electronic control system is given on FIG. 4B. The charge circuit (4.4) receives input current of 110 or 220 volts which is transmitted through the command control (4.5) to the metal contacts of the housing.

Advantageously, the device of the invention is free from cable linking the carrying and control case to the vaginal stimulator and is then pratical to use.

Prior the first use, the device user has only to select the type of incontinence and the wished use time. He has also to make a first charge of the inside vaginal stimulator rechargeable battery (6 hours). To use the vaginal stimulator there is only to open the carrying and control case, remove the vaginal stimulator from its housing, thread a 20 centimeters bit of string in the eyelet, knot the two ends of the string, lubricate the vaginal stimulator and insert it into the vagina. The vaginal stimulator is working. At the end of the session, take the vaginal stimulator out of the vagina, cut and throw away the bit of string, clean the vaginal stimulator, place it back in its resting nest and close the cover of the carrying and control case. The battery will be charge automatically.

What is claimed is:

1. A vaginal stimulator system comprising:
   a stimulator body having first and second conductors for transmitting electrical pulses to the vagina;
   a micro-controller means located in the stimulator body for controlling the application of pulsating signals to the first and second conductors in accordance with programmed instructions corresponding to a particular type of urinary incontinence to be treated;
   a battery power supply located inside the stimulator body connected to the micro-controller means;
   a case for enclosing the stimulator body during non-use of the stimulator body, the case having first and second contacts correspondingly aligned with the first and second conductors of the stimulator body;
   means located in the case for entering instructions regarding current to be applied by the first and second conductors of the stimulator body that stimulate according to the type of urinary incontinence to be treated;
   the micro-controller means in the stimulator body storing the instructions entered in the instruction entering means; wherein
   the first and second contacts are connected to the micro-controller means for unidirectionally inputting signals from the instruction entering means to the micro-controller means via the first and second conductors of the stimulator body.

2. The stimulator system of claim 1 further comprising:
   an eyelet formed at one end of the stimulator body; and
   a guide formed in the stimulator body for guiding a length of string into the eyelet.

3. The stimulator system of claim 1 wherein the means located in the case for entering instructions further comprise control knobs.

4. The stimulator system of claim 1 further comprising:
   a third case contact and a third stimulator body conductor; wherein
   the battery power supply is rechargeable through a charging circuit in the case, the charging circuit being connected to the battery through the second and third case contacts and the corresponding second and third stimulator body conductors, the power supply being recharged when the case is closed, termination of recharging and operation of the stimulator subject to opening of the case.

5. The stimulator system of claim 2 further comprising:
   a projection in the case and received in the eyelet of the stimulator body for positioning the stimulator body in the case so that the conductors of the stimulator body reside in alignment with the contacts of the case.

* * * * *